(12) United States Patent
Langley et al.

(10) Patent No.: US 7,794,430 B2
(45) Date of Patent: Sep. 14, 2010

(54) INJECTION DEVICE

(75) Inventors: Christopher Nigel Langley, Leamington Spa (GB); Robert Woolston, Moreton Morrell (GB)

(73) Assignee: DCA Design International Limited, Warwick (GB)

( * ) Notice: Subject to any disclaimer, the term of this patent is extended or adjusted under 35 U.S.C. 154(b) by 490 days.

(21) Appl. No.: 10/471,721

(22) PCT Filed: Mar. 26, 2002

(86) PCT No.: PCT/GB02/01459

§ 371 (c)(1), (2), (4) Date: Sep. 15, 2003

(87) PCT Pub. No.: WO02/076539

PCT Pub. Date: Oct. 3, 2002

(65) Prior Publication Data

US 2004/0176729 A1 Sep. 9, 2004

(30) Foreign Application Priority Data

Mar. 27, 2001 (GB) ................................ 0107608.2

(51) Int. Cl.
*A61M 37/00* (2006.01)
*A61M 5/00* (2006.01)
(52) U.S. Cl. ...................... 604/155; 604/207
(58) Field of Classification Search ............. 604/131, 604/151, 152, 153, 154, 256, 207–211, 155
See application file for complete search history.

(56) References Cited

U.S. PATENT DOCUMENTS 4,865,591 A * 9/1989 Sams .......................... 604/186

5,226,895 A * 7/1993 Harris ......................... 604/208

(Continued)

FOREIGN PATENT DOCUMENTS

EP 0 446 403 A1 9/1991

(Continued)

*Primary Examiner*—Kevin C Sirmons
*Assistant Examiner*—Andrew M Gilbert
(74) *Attorney, Agent, or Firm*—Oliff & Berridge, PLC

(57) ABSTRACT

Injection devices are known for the self administration of medicament by patients in which the medicaments is typically contained within a cartridge located within the injection device. It is a problem that injection devices should be small enough to fit into a jacket pocket or a hand bag without difficulty. Also, the injection device must be of a size that enables a piston or similar used to drive a cartridge bung within the cartridge to be moved both to a maximum dispense position within the cartridge and to be fully withdrawn from the cartridge to allow for replacement of the cartridge. A drive mechanism for an injection device is disclosed in which a piston (48) is successively moved along the first axis to drive a bung (20) into a medicament cartridge (18), a displacement mechanism comprising a dose setting spindle (30) is disposed along a second axis, the second axis being parallel to the first axis, transmission means connected between the dose setting spindle (30) and the piston (20), and displacement means to displace the dose setting spindle (30) with respect to the medicament cartridge (18), a movement of the displacement means in a first direction causing movement of the dose setting spindle (30) and the piston (20) in the first direction.

10 Claims, 3 Drawing Sheets

U.S. PATENT DOCUMENTS

| | | | |
|---|---|---|---|
| 5,279,585 A * | 1/1994 | Balkwill | 604/207 |
| 5,304,152 A * | 4/1994 | Sams | 604/207 |
| 5,925,021 A * | 7/1999 | Castellano et al. | 604/207 |
| 5,928,201 A * | 7/1999 | Poulsen et al. | 604/208 |
| 6,003,736 A * | 12/1999 | Ljunggren | 222/309 |
| 6,042,571 A * | 3/2000 | Hjertman et al. | 604/208 |
| 6,045,537 A | 4/2000 | Klitmose | 604/224 |
| 6,221,053 B1 * | 4/2001 | Walters et al. | 604/211 |
| 6,796,970 B1 * | 9/2004 | Klitmose et al. | 604/207 |
| 6,972,007 B2 * | 12/2005 | Geiser et al. | 604/211 |
| 2003/0009133 A1 * | 1/2003 | Ramey | 604/155 |
| 2004/0087904 A1 * | 5/2004 | Langley et al. | 604/131 |

FOREIGN PATENT DOCUMENTS

| | | |
|---|---|---|
| EP | 0 778 034 A1 | 6/1997 |
| FR | 2 598 624 | 11/1987 |
| FR | 2 767 479 | 2/1999 |
| WO | WO 98/40167 | 9/1998 |
| WO | WO 98/57688 | 12/1998 |

* cited by examiner

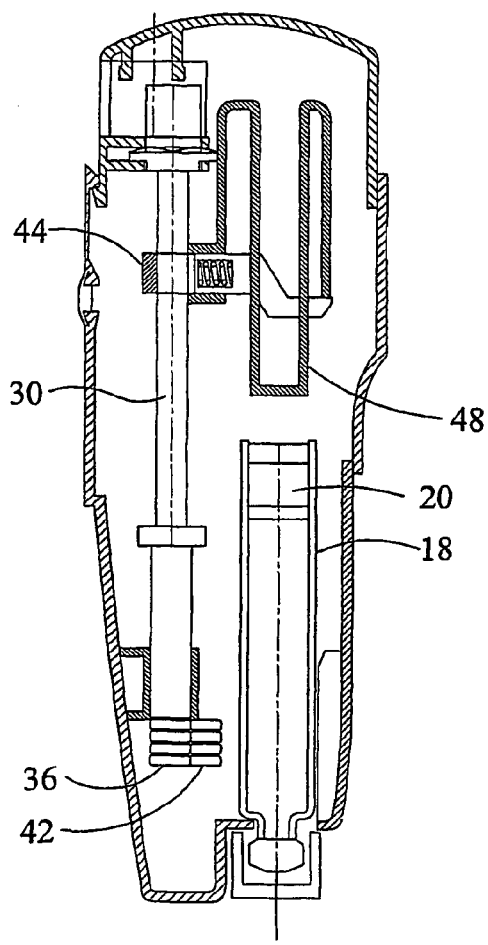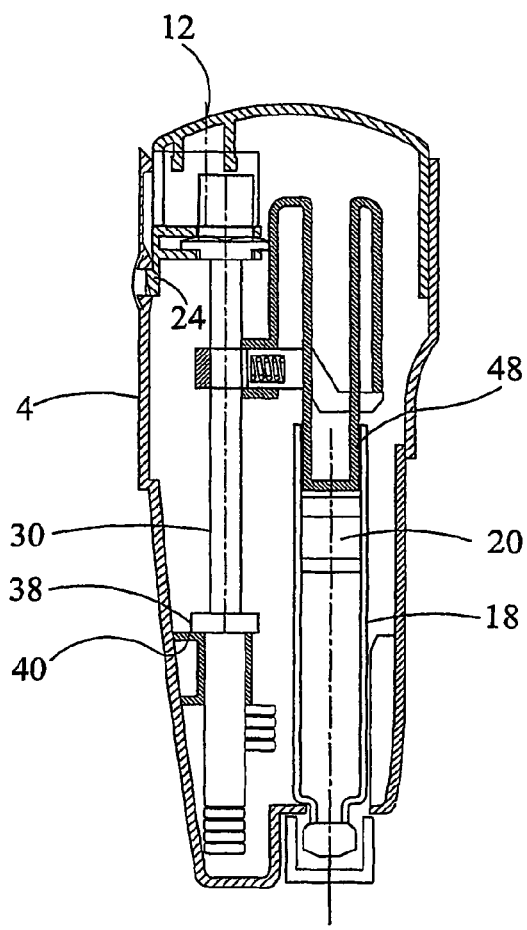
FIG 3
FIG 4

INJECTION DEVICE

The present invention relates to improvements in an injection device, and in particular to improvements in a portable injection device for dispensing controlled quantities of a medicament.

Injection devices are known for the self administration of medicament by patients. For example, those suffering from diabetes may require regular injections of insulin. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This can be a particular problem for the elderly, the infirm, those suffering from vision difficulties and others suffering from diabetes related problems which impair their faculties.

The medicament is typically contained within a cartridge located within the injection device. The cartridge has a bung or piston at one end which is driven towards a second end of the cartridge to expel the medicament from the injection device. It is a problem that injection devices should be small enough to fit into a jacket pocket or a hand bag without difficulty. At the same time, the injection device must be of a size that enables a piston or the like used to drive the cartridge bung within the cartridge to be moved both to a maximum dispense position within the cartridge and to be fully withdrawn from the cartridge to allow for replacement of the cartridge.

It is an advantage of the present invention that it provides a solution to these conflicting requirements.

According to a first aspect of the present invention, a drive mechanism for an injection device in which a piston is successively moved along a first axis in relation to a first end of a medicament cartridge containing a medicament selectively to drive a bung closing a first end of the medicament cartridge into the medicament cartridge to expel medicament through a delivery member located at a second end of the medicament cartridge, in which the displacement mechanism comprises a dose setting spindle disposed along a second axis, the second axis being parallel to the first axis, transmission means connected between the dose setting spindle and the piston, and displacement means to displace the dose setting spindle with respect to the medicament cartridge, a movement of the displacement means in a first direction causing movement of the dose setting spindle and the piston in the first direction.

Preferably the drive mechanism further comprises a dose dial mechanism connected to the dose setting spindle to control the movement of the dose setting spindle. More preferably, the dose setting spindle is connected to the dose dial mechanism by a spline.

Preferably, the piston comprises a sleeve member connected to the drive rack and a piston member located concentrically within the sleeve member and extending outward from the sleeve member.

According to a second aspect of the present invention an injection device having a main housing incorporates a drive mechanism in accordance with the first aspect of the invention.

Preferably, the displacement means comprises a button located for displacement within a housing of the injection device. More preferably, the dose dial mechanism is retained within the button.

Preferably, the injector device further comprises a secondary housing adapted for displacement with respect to the main housing, the secondary housing being provided with a web for abutment with an abutment surface provided on the transmission means in order to allow the piston to be displaced along the first axis in a direction opposite the first direction The invention will now be described, by way of example only, with reference to the accompanying drawings in which:—

FIG. 3 shows a side section similar to FIG. 1 with a dosage of medicament dialed;

FIG. 4 shows a side section similar to FIG. 1 with the dosage delivered;

Like reference numerals will be used to refer to like parts of the injection device.

Figure 1:
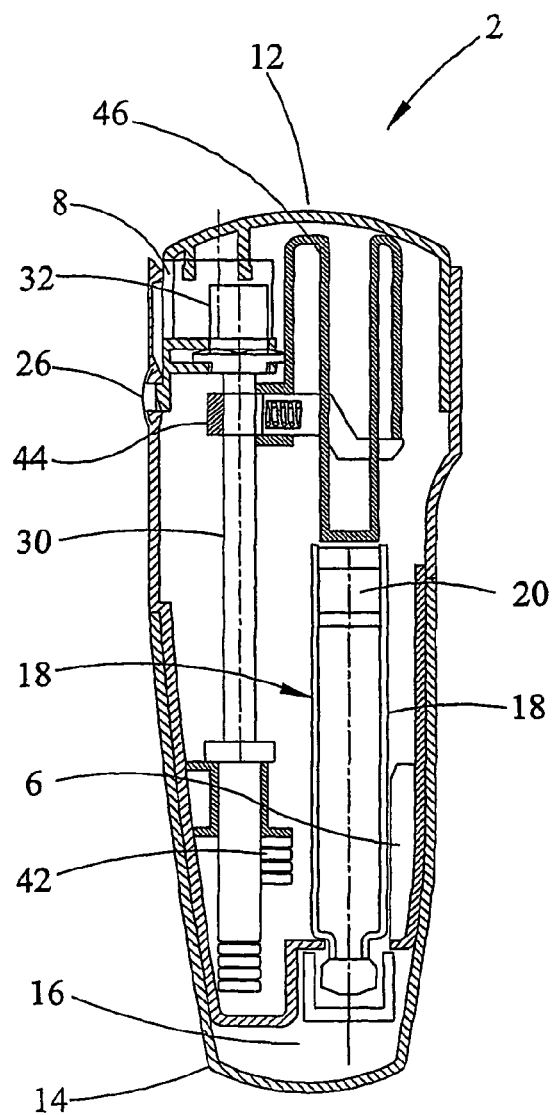
FIG. 1 shows a side section of an injection device having a drive mechanism according to the present invention in which the injection device is closed and a medicament cartridge is full.

Referring first to FIG. 1 there may be seen an injection device 2 in accordance with the present invention. The injection device 2 comprises a main housing 4, a secondary housing 6, a dial dose mechanism 8, a drive mechanism 10, a button 12 and a cover 14. A needle unit 16 including a delivery member in the form a hollow needle is secured to a first end of the main housing 4. A medicament cartridge 18 having a first end and a second end nay be stored in the main housing 4. In the illustrated embodiment, the medicament cartridge 18 is located between the main housing 4 and the secondary housing 6. When the needle unit 16 is in place, the needle unit pierces a flexible membrane at the first end of the medicament cartridge 18. A displaceable bung 20 is located at the second end of the medicament cartridge 18. The cover 14 is provided over the first end of the main housing 4 to protect the needle unit 16 from damage and a user from inadvertent pricking by the needle. The cover 14 also provides a discrete appearance to the injection device 2.

Figure 7:
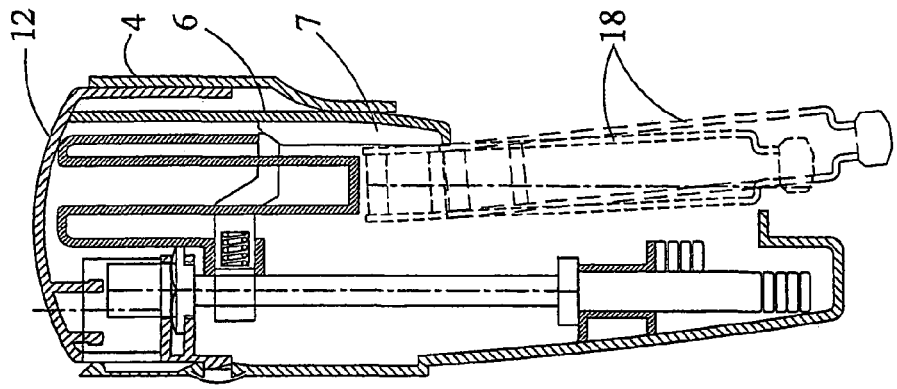
FIG. 7 shows a side section similar to FIG. 1 with the drive mechanism fully withdrawn and a cartridge access cover removed.

The secondary housing 6 is displaceable with respect to the main housing 4 to allow access by a user to the medicament cartridge 18. As can be seen, in the illustrated embodiment, the secondary housing 6 is slidably retractable within the main housing 4 (FIG. 7). The secondary housing 6 is provided with a web 7 extending inwardly of the secondary housing 6.

The button 12 is preferably in the form of a cup adapted for slidable movement within the main housing 4. The main housing 4 and the button 12 are preferably provided with a catch to releasably retain the button 12 in a closed or 'off' position. In the illustrated embodiment the main housing 4 has an opening 22 into which extend a finger 24 from the button 12 and a flexible tab or cap 26. The cap 26 and the finger 24 normally each extend part way through the opening 22. Pushing of the cap 26 pushes the finger 24 from the opening releases the button 12. When the pressure on the cap 26 ceases the cap 26 will revert to the previous position so as to allow the finger 24 to enter the opening 22 following depression of the button 12. The finger 24 may be used to engage a lip 28 on the main housing 4 to retain the button 12 within the main housing 4.

The dose dial mechanism 8 is located in the button 12. When the button 12 is in the fully depressed position, the dial dose mechanism 8 is obscured from view. On release of the button 12, the dial dose mechanism 8 is exposed for manipulation by a user to set a required dosage.

A dose setting spindle 30 is connected at a first end by a spline 32 to the dose dial mechanism 8. The dose setting spindle 30 is provided with a threaded portion. A counter rod 34 extends from a second end of the dose setting spindle 30. A radially extending flange 38 is also provided at a second end of the dose setting spindle 30. In the closed position the radially extending flange 38 abuts an abutment surface 40 provided in the main housing 4.

The main housing 4 is also provided with a first set of counter contacts 42. When the injection device 2 is in a 'ready' position, counter contacts 36 on the counter rod 34 marry or match up with the first set of counter contacts 42 in the main housing 4.

A drive means is provided carried from the dose setting spindle 30. The drive means comprises a drive rack 44 in the form of a member having a threaded bore. The drive rack 44 is carried from the thread of the dose setting spindle 30 such that rotation of the dose setting spindle 30 causes the drive rack 44 to precess along the dose setting spindle 30. The drive rack 44 is connected to a piston 46. In a fully withdrawn position, the drive rack 44 is located on the dose setting spindle 30 adjacent the dose dial mechanism 8. The piston 46 comprises a piston member 48 located concentrically within a sleeve member 50 and extending outward from the sleeve member 50, such that in use, the sleeve member 50 passes outside of the medicament cartridge 18 and the piston member 48 passes within the medicament cartridge 18 to abut and drive the displaceable medicament cartridge bung 20. As can be seen the piston 46 and the medicament cartridge 18 are disposed along a first axis.

In the fully withdrawn position, the rearmost surface of the piston 46 may abut an inner surface of the button 12.

Figure 2:
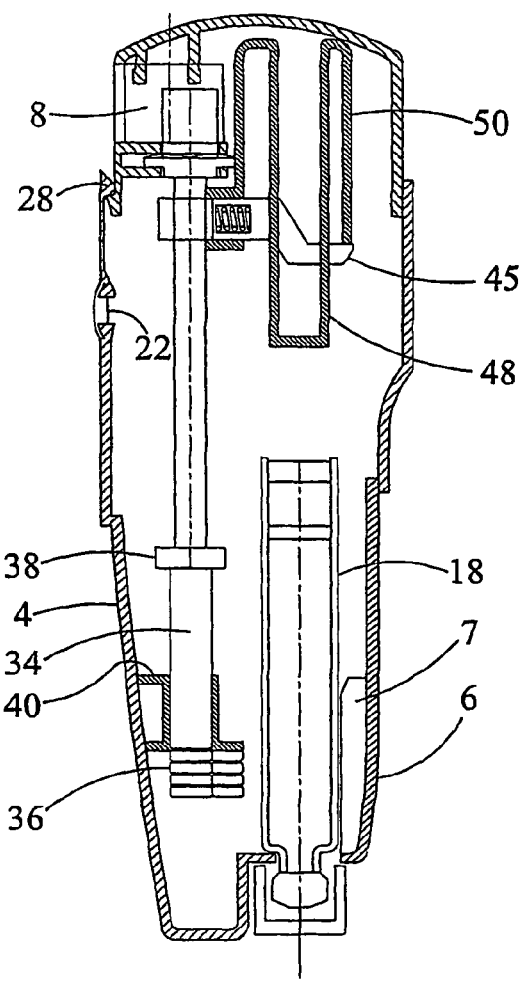
FIG. 2 shows a side section similar to FIG. 1 with the injection device ready for use.

To operate the injection device 2 a user first releases the button 12 in the manner described to cause the button 12 to move to the 'ready' position (FIG. 2). The dose dial mechanism 8 can now be operated to rotate the dose setting spindle 30. This has the effect of causing the drive rack 44 to precess along the dose setting spindle 30 by a given distance (FIG. 3). This distance corresponds to the displacement of the cartridge bung 20 required to dispense a required amount of medicament. The counter contacts 36,42 can be used to measure rotation of the dose setting spindle 30 which in turn gives an accurate guide as to how far the drive rack 44 has moved. The dial dose mechanism including the dose setting spindle 30 and the drive rack 44 are disposed along a second axis. The second axis is disposed parallel to the first axis.

The button 12 is then depressed driving the piston member 48 into the displaceable bung 20 of the medicament cartridge 18 until the radially extending flange 38 of the dose setting spindle 30 again abuts the abutment surface 40 of the main housing 4. In this position, the finger 24 of the button 12 will once again extend through the opening 22 in the main housing 4 (FIG. 4).

Figure 5:
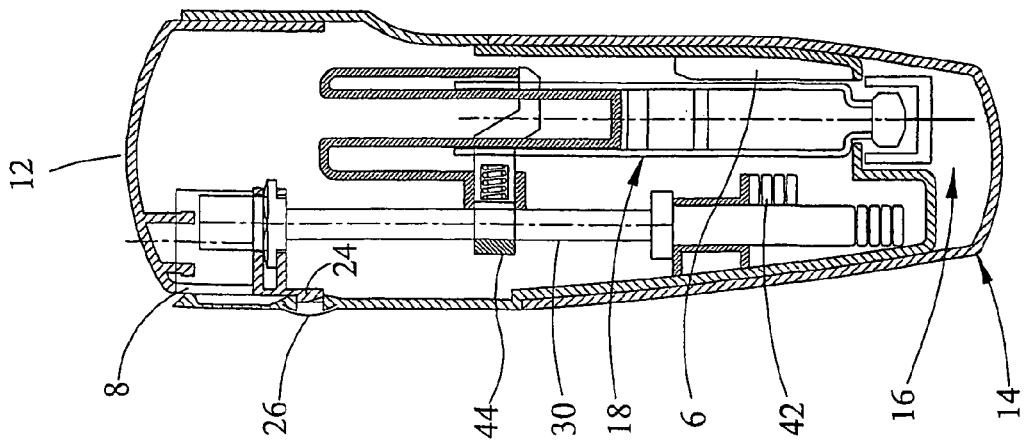
FIG. 5 shows a side section similar to FIG. 1 with the injection device closed and the medicament cartridge half full.

On the next use of the injection device 2, the piston member 48 is at least partially withdrawn from the medicament cartridge 18 since the piston 46 together with the piston member 48 is drawn with the button 12 away from the first end of the main housing 4. A new dose is set, precessing the drive rack 44 further along the dose setting spindle 30 prior to depression of the button 12. As the process is repeated the drive rack 44 precesses yet further along the dose setting spindle 30 (FIG. 5).

Figure 6:
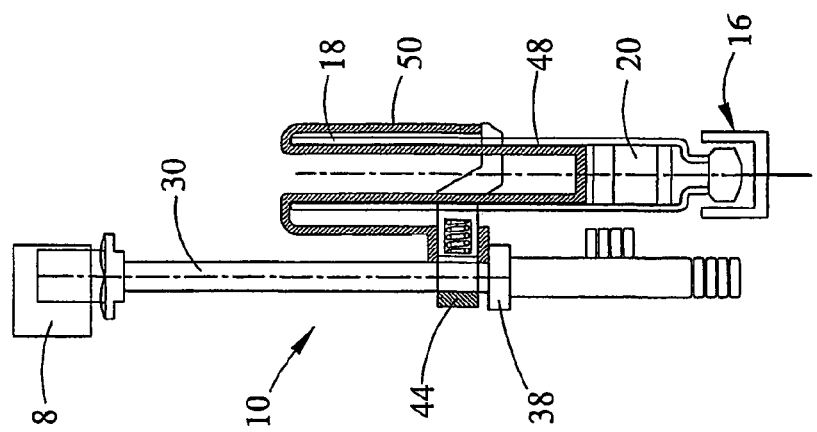
FIG. 6 shows a side section of the drive mechanism of FIG. 1 with the medicament cartridge empty.

This process may be repeated until the medicament cartridge 18 is empty, the medicament cartridge 18 contains insufficient medicament to deliver the dialed dose or some other condition is met. For example, the drive rack 44 may abut the radially extending flange 38 on the dose setting spindle 30 and precess no further, the dose setting spindle 30 being of a suitable length such that the drive rack 44 will abut the radially extending flange 38 when the displaceable bung 20 can travel no further within the medicament cartridge 18 (FIG. 6).

The piston member 48 may then be withdrawn to allow replacement of the medicament cartridge 18. In the illustrated embodiment, this occurs in the following manner. A user displaces the secondary housing away front the first end of the main housing 4 along a third axis. The third axis is substantially parallel to the first axis and the second axis. As the secondary housing 6 is moved, the web 7 abuts with an abutment surface 45 provided for this purpose on the drive rack 44. Further movement of the secondary housing 6 moves the drive rack 44, together with the piston 46 along the first axis away from the first end of the main housing 4, thereby removing the piston 46 from within the medicament cartridge 18. Thus, when the secondary housing has been fully displaced as shown in FIG. 7, the piston 46 has been withdrawn from the medicament cartridge 18 and the user is free to remove the medicament cartridge 18 and replace the medicament cartridge 18 as required.

The injection device 2 described has among its advantages that it is relatively simple to assemble and has relatively few moving parts. The counter contacts 36,42 allow the angular position of the dose setting spindle 30 to be determined, thus allowing for calculation of the precise location of the piston member 48. Further, since the dose dial mechanism 8 is hidden until release of the button 12, the dial dose mechanism 8 cannot be tampered with while the button 12 is depressed.

Also, in comparison with known pen type injectors in which the piston and a drive means for successively displacing the piston are located along a single axis a more compact design of pen type injector is provided for in the present invention.

The relative arrangement of the drive mechanism and the medicament cartridge means that the main housing provides a relatively large flat face where a relatively large dose display, such as a liquid crystal display may be located. This in turn enables the dose display to use relatively large figures or other characters. This is an advantage for those with impaired vision.

The invention claimed is:

1. A drive mechanism for an injection device in which a piston is successively moved along a first axis in a first longitudinal direction in relation to a first end of a medicament cartridge containing a medicament selectively to drive a bung closing the first end of the medicament cartridge into the medicament cartridge to expel medicament through a delivery member located at a second end of the medicament cartridge, the first axis being a central longitudinal axis of the medicament cartridge, wherein a displacement mechanism comprises a dose setting spindle disposed along a second axis around which the dose setting spindle is rotatable, the second axis being parallel to the first axis and the second axis being separate from the first axis, a transmission means connected between the dose setting spindle and the piston, and a displacement means to displace the dose setting spindle with respect to the medicament cartridge, a movement of the displacement means in the first longitudinal direction causing movement of the dose setting spindle and the piston in the first longitudinal direction.

2. A drive mechanism for an injection device according to claim 1, wherein the drive mechanism further comprises a dose dial mechanism connected to the dose setting spindle to control rotational movement of the dose setting spindle.

3. A drive mechanism for an injection device according to claim 2, wherein the dose setting spindle is connected to the dose dial mechanism by a spline.

4. A drive mechanism for an injection device according to claim 1, wherein the transmission means comprises a drive rack.

5. A drive mechanism for an injection device according to claim 1, wherein the piston comprises a sleeve member connected to a drive rack and a piston member located concentrically within the sleeve member and extending outward from the sleeve member.

6. A drive mechanism for an injection device according to claim 1, wherein the dose setting spindle is provided with counter contacts.

7. An injection device having a main housing incorporating a drive mechanism according to claim 1.

8. An injection device according to claim 7, wherein the displacement means comprises a button located for displacement within a housing of the injection device.

9. An injection device according to claim 8, wherein a dose dial mechanism is retained within the button.

10. An injection device according to claim 7, the injection device further comprising a secondary housing adapted for displacement with respect to the main housing, wherein the secondary housing is provided with a web for abutment with an abutment surface provided on the transmission means in order to allow the piston to be displaced along the first axis in a direction opposite the first longitudinal direction.

* * * * *